US011419828B2

(12) United States Patent
Stark

(10) Patent No.: US 11,419,828 B2
(45) Date of Patent: Aug. 23, 2022

(54) HAIR CARE TERPINEN 4-OL (T4O) COMPOSITION FOR THE TREATMENT OF DEMODEX MITES ON SCALP

(71) Applicant: Ira Mark Stark, Concord, CA (US)

(72) Inventor: Ira Mark Stark, Concord, CA (US)

( * ) Notice: Subject to any disclaimer, the term of this patent is extended or adjusted under 35 U.S.C. 154(b) by 6 days.

(21) Appl. No.: 17/151,161

(22) Filed: Jan. 16, 2021

(65) Prior Publication Data
US 2022/0226256 A1 Jul. 21, 2022

(51) Int. Cl.
| | | |
|---|---|---|
| *A61K 31/045* | (2006.01) | |
| *A61K 36/889* | (2006.01) | |
| *A61K 36/53* | (2006.01) | |
| *A61K 36/61* | (2006.01) | |
| *A61K 36/534* | (2006.01) | |
| *A61K 47/26* | (2006.01) | |
| *A61K 9/00* | (2006.01) | |
| *A61K 36/886* | (2006.01) | |

(Continued)

(52) U.S. Cl.
CPC .......... *A61K 31/045* (2013.01); *A61K 9/0014* (2013.01); *A61K 31/047* (2013.01); *A61K 31/522* (2013.01); *A61K 36/185* (2013.01); *A61K 36/484* (2013.01); *A61K 36/53* (2013.01); *A61K 36/534* (2013.01); *A61K 36/61* (2013.01); *A61K 36/82* (2013.01); *A61K 36/886* (2013.01); *A61K 36/889* (2013.01); *A61K 47/12* (2013.01); *A61K 47/26* (2013.01)

(58) Field of Classification Search
CPC ...... A61K 2300/00; A61K 31/60; A61K 8/35; A61K 45/06; A61K 8/498; A61K 9/0014; A61K 35/74; A61K 31/045; A61K 9/08; A61K 36/61; A61K 31/205; A61K 31/7008; A61K 31/728; A61K 8/345; A61K 31/122; A61K 31/4166; A61K 8/342; A61K 47/26; A61K 8/602; A61K 9/0075; A61K 9/02; A61K 31/07; A61K 31/222; A61K 31/30; A61K 31/315; A61K 31/4168; A61K 31/59; A61K 33/30; A61K 8/347; A61K 8/355; A61K 8/55; A61K 8/99; A61K 9/0048; A61K 9/2054; A61K 9/4866; A61K 36/324; A61K 31/42; A61K 31/422; A61K 31/55; A61K 31/683; A61K 9/0043; A61K 9/0053; A61K 9/2009; A61K 9/2013; A61K 9/4858; A61K 31/4164; A61K 31/695; A61K 47/02; A61K 31/27; A61K 31/35; A61K 31/473; A61K 31/661; A61K 31/704; A61K 36/185; A61K 9/0019; A61K 9/0073; A61K 9/06; A61K 9/10; A61K 9/12; A61K 9/4825; A61K 2800/28; A61K 31/357; A61K 36/28; A61K 47/36; A61K 8/49; A61K 2800/10; A61K 2800/88; A61K 31/10; A61K 31/203; A61K 31/327; A61K 31/37; A61K 31/4412; A61K 31/4706; A61K 31/573; A61K 31/662; A61K 31/7004; A61K 33/34; A61K 33/38; A61K 35/741; A61K 36/484; A61K 38/49; A61K 8/18; A61K 8/27; A61K 8/362; A61K 8/368; A61K 8/38; A61K 8/4913; A61K 8/67; A61K 8/671; A61K 8/9728; A61K 8/9789; A61K 9/0031; A61K 9/0046; A61K 2035/115; A61K 31/14; A61K 31/325; A61K 31/343; A61K 31/36; A61K 31/404; A61K 31/4178; A61K 31/4184; A61K 31/445; A61K 31/47; A61K 31/4748; A61K 31/664; A61K 31/675; A61K 31/685; A61K 31/7048; A61K 33/00; A61K 35/08; A61K 36/37; A61K 38/47; A61K 47/12; A61K 47/22; A61K 47/38; A61K 8/375; A61K 8/64; A61K 9/0017; A61K 9/0078; A61K 9/107; A61K 9/16; A61K 9/2004; A61K 9/2027; A61K 9/2059; A61K 9/48; A61K 9/50; A61K 2236/00; A61K 2236/10; A61K 2236/35; A61K 2800/30; A61K 2800/412; A61K 2800/432; A61K 2800/5922; A61K 2800/70; A61K 2800/74; A61K 2800/805; A61K 2800/85; A61K 31/196; A61K 31/216; A61K 31/245; A61K 31/415; A61K 36/899; A61K 47/10; A61K 47/14; A61K 47/20; A61K 47/42; A61K 8/0241; A61K 8/046; A61K 8/11; A61K 8/19; A61K 8/361; A61K 8/37; A61K 8/41; A61K 8/416; A61K 8/43; A61K 8/492; A61K 8/4926; A61K 8/4946; A61K 8/63; A61K 8/66; A61K 8/731; A61K 8/922; A61K 8/9794; A61K 9/0034; A61K 9/0036; A61K 9/0039; A61K 9/0056; A61K 9/006; A61K 9/008; A61K 9/127; A61K 9/14; A61K 9/1605; A61K 9/5005; A61K 9/5015; A61K 9/7007; A61K 9/7015; A61P 33/14; A61P 17/08; A61P 33/00; A61P 33/10; A61P 17/14; A61P 43/00
See application file for complete search history.

(56) References Cited

FOREIGN PATENT DOCUMENTS

WO WO-2014167552 A1 * 10/2014 ........... A61K 36/235

* cited by examiner

*Primary Examiner* — Aaron J Kosar

(57) ABSTRACT

The present invention is a hair care compositions, and more particularly to hair care compositions that contain a novel blend of natural ingredients which can be applied to the scalp and/or hair of a user for the treatment of scalp demodex which inturn helps to prevent hair loss and stimulates hair growth on male scalp. The composition includes at least one essential oil, a carrier oil and additives. One of the (Continued)

essential oils included is tea tree oil, the active ingredient of which is Terpinen-4-ol solution (T40).

5 Claims, No Drawings

(51) Int. Cl.
*A61K 36/185* (2006.01)
*A61K 36/484* (2006.01)
*A61K 31/522* (2006.01)
*A61K 31/047* (2006.01)
*A61K 47/12* (2006.01)
*A61K 36/82* (2006.01)

HAIR CARE TERPINEN 4-OL (T4O) COMPOSITION FOR THE TREATMENT OF DEMODEX MITES ON SCALP

FIELD OF THE INVENTION

The present invention relates to hair care compositions, and more particularly to hair care compositions that contain a novel blend of natural ingredients which can be applied to the scalp and/or hair of a user for the treatment of scalp demodex which inturn helps to prevent hair loss and stimulates hair growth on male scalp.

BACKGROUND OF THE INVENTION

*Demodex*, a genus of tiny parasitic mites that live in or near hair follicles of mammals, are among the smallest of arthropods with two species *Demodex folliculorum* and *Demodex brevis* typically found on humans.

*Demodex* mite is an obligatory human ecto-parasite, and it is resident in or near the pilo-sebaceous units. About 65 species of *Demodex* are known. Two species *D. folliculorum* and *Demodex brevis*, collectively referred to as *Demodex*, are typically found on humans, occurring in 10% of skin biopsies and 12% of follicles.

*Demodex* is an ecto-parasite of pilo-sebaceous follicle and sebaceous gland, typically found on the face including cheeks, nose, chin, forehead, temples, eye lashes, brows, and also on the balding scalp, neck and ears. Other seborrheic regions such as naso-labial folds, peri-orbital areas, and less commonly upper and medial region of chest and back are also infested. They may also be found on penis, mons veneris, buttocks, and in the ectopic sebaceous glands in the buccal mucosa.

The mites are transferred between hosts through contact of hair, eyebrows, and sebaceous glands on the nose.

*Demodex* mites are resistant to a wide range of antiseptic agents including 75% alcohol, 10% povidone-iodine, and erythromycin. The most effective and commonly used treatment agent for *Demodex* is tea tree oil. Tea tree oil is currently the go-to in-office and at-home treatment option for *Demodex*. Terpinen-4-ol—a terpene with antimicrobial, antifungal, antiviral, antiseptic, and acaricidal properties—is the active ingredient in tea tree oil.

Terpinen-4-ol has acetylcholinesterase-inhibiting effects that produce the acaricidal effect which leads the mite to exit the hair follicle and migrate onto the skin before mating. Studies have demonstrated that as low as 5% concentration (when applied to the lids twice daily) and as high as 50% concentration (when applied once weekly) of tea tree oil are effective at reducing *Demodex* infestation when applied to the lids and base of the eyelash follicle. A 38% concentration of terpinen-4-ol has been shown to reduce *Demodex* effectively over a period of 4 weeks.

Tea tree oil (TTO) is a natural essential oil steam-distilled from the Australian native plant *Melaleuca alternifolia*. Studies showed that Terpinen-4-ol is the most active ingredient in TTO in exerting *Demodex* mite-killing effects. Further, other studies have shown that Terpinen-4-ol (T4O) is also the most active ingredient in TTO to exert antibacterial and antifungal effects.

The use of herbal products including essential oils or carrier oils provides benefits over and above the aforementioned synthetic chemicals, etc. Essential Oils contained in plants have a very beneficial effect on hair growth. Studies suggest that one or more of the essential oils are biologically able to promote hair growth. Essential oils for hair growth are excellent for cleansing, nourishing, and strengthening the hair follicle and shaft. These essential oils for hair growth stimulate the hair follicles to grow faster than the hair would normally.

Since, most essential oils are highly concentrated and potent, they may have adverse effect on skin if used undiluted. It is ideal to dilute essential oils with carrier oils. Carrier oils are a vegetable origin extracted from nuts and seeds by cold pressing. Carrier oils provide lubrication and moisture and help with the absorption of essential oils into the skin. Moreover, carrier oils alone also provide nutrition and moisture to dry or damaged hair.

Taking into account the above considerations, the present invention provides for a Terpinen-4-ol hair care composition for *Demodex* treatment of scalp apart from providing nourishment to the scalp and hair and stimulating growth of hair.

SUMMARY OF THE INVENTION

In an aspect of the present invention, there is disclosed a hair care composition being formulated for application on users' scalp either as a shampoo or spray. The composition comprises one and/or more carrier oil, one and/or more essential oil, The carrier oils may be selected from a group consisting of Fractionated coconut oil, and any combinations thereof. The essential oils may be selected from a group consisting of Eucalyptus essential oil, Peppermint essential oil, Lavender essential oil, Tea Tree essential oil, and any combinations thereof. The additives selected may be from Saw Palmetto Extract, Green Tea Extract, aloe Vera Pure juice, nettle Leaf extract, licorice Root extract, caffeine powder, copper peptides menthol crystals, Propanediol 1,3, citric acid, potassium sorbate & Benzyl alcohol.

The synergistic effect of the ingredients of hair care composition of the present invention has demonstrated that they can help in the treatment of *Demodex* of scalp, strengthen hair, prevent hair loss and promote hair growth.

In another aspect of the present invention the hair care composition comprises:

Water 48% by volume or 480 grams by weight, Witch Hazel Hydrosol of about 20.00% by volume or 200 grams by weight, Terpinen-4-ol solution (T4O) of about 5.00% by volume or 50 grams by weight, Carrier Oil: Fractionated coconut oil of about 2.00% by volume or 20 grams by weight, Essential Oils: Lavender Oil about 0.20% by volume or 2.0 grams by weight; Eucalyptus Oil about 0.20% by volume or 2.0 grams by weight; Peppermint Oil 0.60% by volume or 6.0 grams by weight, Polysorbate 80 about 7.00% by volume or 70.0 grams by weight.

Additives include: Saw Palmetto Extract about 2.00% by volume or 20.0 grams by weight; Green Tea Extract about 1.00% by volume or 10.0 grams by weight; Aloe Vera Pure Juice about 3.00% by volume or 30.0 grams by weight; Nettle Leaf Extract of about 2.00% by volume or 20.0 grams by weight; Licorice Root Extract of about 1.00% by volume or 10.0 grams by weight; Caffeine Powder of about 0.50% by volume or 5.0 grams by weight; Copper Peptides GHK of about 0.20% by volume or 2.0 grams by weight; Menthol Crystals of about 1.00% by volume or 10.0 grams by weight; Propanediol 1,3 of about 5.00% by volume or 50.0 grams by weight; Citric Acid of about 0.10% by volume or 1.00 grams by weight; Potassium sorbate of about 0.20% by volume or 2.00 grams by weight; Geogard 221—(Benzylaicohol-DHA) of about 1.00% by volume or 10.0 grams by weight.

The hair care composition according to a still further aspect of the present invention comprises: Water 38% by volume or 380 grams by weight, Witch Hazel Hydrosol of about 20.00% by volume or 200 grams by weight, Terpinen-4-ol solution (T4O) of about 10.00% by volume or 100 grams by weight, Carrier Oil: Fractionated coconut oil of about 2.00% by volume or 20 grams by weight, Essential Oils: Lavender Oil about 0.20% by volume or 2.0 grams by weight; Eucalyptus Oil about 0.20% by volume or 2.0 grams by weight; Peppermint Oil 0.60% by volume or 6.0 grams by weight, Polysorbate 80 about 12.00% by volume or 120.0 grams by weight.

Additives include: Saw Palmetto Extract about 2.00% by volume or 20.0 grams by weight; Green Tea Extract about 1.00% by volume or 10.0 grams by weight; Aloe Vera Pure Juice about 3.00% by volume or 30.0 grams by weight; Nettle Leaf Extract of about 2.00% by volume or 20.0 grams by weight; Licorice Root Extract of about 1.00% by volume or 10.0 grams by weight; Caffeine Powder of about 0.50% by volume or 5.0 grams by weight; Copper Peptides GHK of about 0.20% by volume or 2.0 grams by weight; Menthol Crystals of about 1.00% by volume or 10.0 grams by weight; Propanediol 1,3 of about 5.00% by volume or 50.0 grams by weight; Citric Acid of about 0.10% by volume or 1.00 grams by weight; Potassium sorbate of about 0.20% by volume or 2.00 grams by weight; Geogard 221—(Benzylalcohol-DHA) of about 1.00% by volume or 10.0 grams by weight.

In another aspect of the present invention the processing method of the above composition is described comprising the steps of:

Placing the water in the container or beaker with continuous agitation, until its total dilution;

Adding Caffeine Powder, Copper Peptides GHK and Potassium sorbate and mixing;

Adding the Menthol Crystals (Previously diluted in Propanediol 1,3) and mixing;

Adding the extracts and other additives in agitation medium;

Continuing mixing until a homogeneous mixture is obtained;

adding the Essential oils, Oils and the Polysorbato 80 in another container and mixing continuously until a homogeneous mixture is obtained;

Slowly adding the oil mixture (Essential oils+Oil+Polysorbato 80) in the Toner;

Mixing continuously until obtaining a homogeneous mixture.

In another aspect of the present invention, the pH of the mixture is maintained at a range of 4.5 to 6.

In a still further aspect of the present invention the pH can be regulated with one or two drops of citric acid (Solution 50%), stirring to mix well.

It is to be understood that the aforementioned components and percentage are only exemplary and that various arrangements are possible in other embodiments.

The more important features of the invention have thus been outlined in order that the more detailed description that follows may be better understood and in order that the present contribution to the art may better be appreciated. Additional features of the invention will be described hereinafter and will form the subject matter of the claims that follow.

The invention is capable of other embodiments and of being practiced and carried out in various ways. Also it is to be understood that the phraseology and terminology employed herein are for the purpose of description and should not be regarded as limiting.

DESCRIPTION OF THE PREFERRED EMBODIMENT

In an exemplary embodiment of the present invention, there is disclosed a hair care product composition being formulated for topical application on users' scalp. The composition comprises one and/or more carrier oil, one and/or more essential oil, and one and/or more additives. The carrier oils may be selected from Fractionated Coconut oil. The essential oils may be selected from a group consisting of Eucalyptus essential oil, Peppermint essential oil, Lavender essential oil, Tea Tree essential oil, and any combinations thereof. The extracts and additives may be selected from a group-consisting of Saw Palmetto Extract, Green TeaExtract, aloe Vera Pure juice, nettle Leaf extract, licorice Root extract, caffeine powder, and any combinations thereof.

Fractionated Coconut oil work as lubricant and moisturizer, as well as carrier oil for essential oils and aids in the delivery of their healing properties without irritation. They are beneficial to the dry and damaged hair and/or skin and promote hair growth.

As is known from studies the ingredients of the hair composition have the following properties:

Witch Hazel Hydrosol: There are many species of witch hazel, but *Hamamelis virginiana* is the one which is used. Constituents of the bark and leaves of *Hamamelis virginiana* are enumerated below:

Polyphenols—The leaves contain up to, but not more than 3%, tannins whereas the cortex/bark of the stems contains up to 12%, but not less than 4%, tannins.

Leaf tannins are a mixture of gallic acid (10%), hydrolysable hamarnelitannin (1.5%) and condensed proanthocyanidins (88.5%). Bark tannins are similar qualitatively, but have a much greater hamamelitannin concentration (up to 65% of ahydroalcoholic extract). Other polyphenols include phenolic acids and flavonoids. At least 27 phenolic constituents have been identified. The flavonoids in the leaves include galactosides and glucuronides and other flavonoids such as kaempherol, quercetin, quercitrin, and isoquercitrin. The Catechins include (+)-catechin, (+)-gallocatechin, (−)-epicatechin gallate(III), and (−)-epigallocatechin gallate(III).

Volatile oil—Both bark and leaves contain volatile oil (0.1% and 0.01% to 0.05%, respectively). The composition of the volatile fraction comprises of about 175 identified compounds in the leaves and 168 compounds in the bark of which the dominating substances are represented by a homologous series of alkanes, alkenes, aliphatic alcohols, related aldehydes, ketones, and fatty acid esters. The volatile oil contains hexane-2-ol, hexenol, α- and β-ionones, eugenol, safrole (maximum 0.2% of the volatile oil) and sesquiterpenes. Other constituents include gallic acid.

The presence of gallic acid and tannins, confer on Witch hazel the anti-inflammatory properties. The antioxidants present help in preventing widespread inflammation and neutralizes free radicals.

Terpinen-4-ol solution (T4O): Terpinen-4-ol, the main component of the essential oil of *Melaleuca alternifolia* (tea tree oil), suppresses inflammatory mediator production by activated human monocytes. Some of, the components of tea tree oil previously shown to have anti-bacterial properties, e.g. terpinen-4-ol and a-terpineol, are also anti-inflammatory in vivo.

Study suggests that tea tree oil may potentially control inflammatory responses to foreign antigens in the skin. With application of tea tree oil to skin, toxicity would be limited and the anti-inflammatory water-soluble components may penetrate into the vascularised dermis and regulate inflammatory processes.

Terpinen-4-ol solution (T4O): Terpinen-4-ol, is a naturally occurring monoterpene and is the main bioactive component of tea-tree oil and is responsible for its antimicrobial and anti-inflammatory properties is Terpinen-4-ol. Typically, there is about 40 percent of Terpinen-4-ol present in Tea Tree Oil.

Tea Tree Oil is particularly adept at helping to quell the itchiness and flakiness. In addition to helping soothe an irritated scalp, Tea Tree Oil may also help support healthier, more robust future hair growth by keeping the hair follicles on the scalp unclogged—and helping to maximize their productivity.

Fractionated coconut oil: The coconut oil contains 92% of saturates consisting of medium chain fatty acids in the form of triglycerides, and about 8% of unsaturates consisting of oleic and linoleic acids as triglycerides. It has small amounts of tocopherols and tocotrienols and phytosterols. It is known to have antiviral and antibacterial effects and excellent healing properties.

Coconut oil is a fat consisting of about 90% saturated fat. The oil contains predominantly triglycerides with 86.5% saturated fatty acids, 5.8% monounsaturated fatty acids, and 1.8% polyunsaturated fatty acids. Of the saturated fatty acids, coconut oil is primarily 44.6% lauric acid, 16.8% myristic acid and 8.2% palmitic acid, although it contains seven different saturated fatty acids in total. Its only monounsaturated fatty acid is oleic acid while its only polyunsaturated fatty acid is linoleic acid.

Both regular and fractionated coconut oils are great sources of medium-chain triglycerides (MCTs), providing fatty acids that contain 6 to 12 carbon atoms. While the main fatty acid in coconut oil is the 12-carbon lauric acid (C12), in fractionated coconut oil most or all of this fatty acid has been removed. The long-chain fatty acids present in coconut oil have also been eliminated. Thus, the main medium-chain fatty acids (MCFAs) in fractionated coconut oil are:

C8: caprylic acid or octanoic acid
C10: capric acid or decanoic acid

Lavender Essential Oil: Lavender belongs to the Labiatae family, which includes ~30 species of *Lavandula*. *Lavandula officinalis* is used in this invention. Lavender oil is one of the most valuable aromatherapy oils, its anti-bacterial and anti-fungal activities can be explained by main components such as linalool, linalyl acetate, lavandulol, geraniol, or eucalyptol.

Among them, linalool has been demonstrated to be the strongest active ingredient against a wide range of microorganisms. Borneol and eucalyptol have also been identified as the main compounds in the many essential oils exhibiting anti-parasitic activity. Terpinen-4-ol, α-pinene, β-pinene, 1,8-cineol, linalool, and 4-terpineol also showed high anti-fungal activity against Gram-positive and Gram-negative strains. Studies have shown that Linalool and linalyl acetate have local anaesthetic effects. Various monoterpenoids, such as α-terpineol, terpinen-4-ol, eucalyptol, and linalool, have antiviral whereas Eucalyptol, terpinen-4-ol, thymol, and carvacrol also have extensive anti-inflammatory effects.

Eucalyptus Essential Oil: The chemical composition of the essential oils extracted from Eucalyptus species (*E. maideni; E. astrengens; E. cinerea; E. leucoxylon; E. lehmani; E. sideroxylon; E. bicostata*) is presented in Table 2. All essential oils contain α-pinene, 1,8-cineol and pinocarveol-trans for all Eucalyptus species studied. The 1,8-cineol was the major compound in all species.

The results revealed that the essential oils showed antibacterial activity with varying.

Peppermint Essential Oil: Botanically, peppermint (*Mentha piperita* L.) belongs to the Lamiaceae family in the genus *Mentha*. The main constituents of the peppermint leaves essential oil includes menthol, menthone, menthofuran, 1,8-cineole, and menthyl acetate. Peppermint oil also has mild antimicrobial and antifungal properties. Like other essential oils, peppermint oil can help stimulate hair growth because of its ability to increase blood circulation around the scalp. When blood circulates, the nutrients from your body can feed your hair follicles more effectively.

Polysorbate 80: It is a non-ionic, multi-purpose emulsifier (enables water and oil to mix). The emulsifying efficacy is increased when combined with cetyl alcohol or sorbitan stearate. It acts as dispersing agent and anti-static thickener and is very useful as solubilizer and stabilizer of essential oils. It may be useful as hair growth supplement.

Saw Palmetto Extract: Saw palmetto (SP, *Serona repens*) is an extract from the berries of the saw palmetto palm tree (American dwarf tree) containing phytosterols (β-sitosterol), fatty acids, β-carotene, and polysaccharides. SP is a competitive, nonselective inhibitor of both forms of 5α-reductase. SP blocks nuclear uptake of DHT in target cells and decreases DHT binding to androgen receptors by approximately 50%. Additionally, the extract increases 3α-hydroxysteroid-dehydrogenase activity, increasing the conversion of DHT to its weaker metabolite, and rostanediol. As a result, the pharmacodynamic profile of SP differs from finasteride due to multiple sites of action.

Green Tea Extract: Fresh green tea leaves contain five major catechins: catechin (C), (−)-epicatechin (EC), (−)-epicatechin 3-gallate (ECG), (−)-epigallocatechin (EGC) and (−)-epigallocatechin gallate (EGCG). The epigallocatechin gallate (EGCG) in green tea may prevent hair loss by inhibiting the activity of hormones that induce hair loss and promoting hair regrowth by stimulating hair follicles.

Aloe Vera Pure Juice: A. vera gel consists mainly of water (>98%) and polysaccharides, including pectins, cellulose, hemicellulose, glucomannan, and acemannan, the latter being considered as the main functional component of A. vera gel, formed from a long chain of acetylated mannose. Aloe vera contains 200 potentially active constituents: vitamins, enzymes, minerals, sugars, lignin, saponins, salicylic acids and amino acids, which are responsible for the multifunctional activity of Aloe.

Vitamins: It contains Vitamins A (beta-carotene), C and E, which are antioxidants which neutralizes free radicals. It also contains Vitamin B12, folic acid, and choline. The vitamins A, C, and E contribute to cell turnover, promoting healthy cell growth and shiny hair. Vitamin B12 and folic acid can keep hair from falling out.

It also comprises, a glycoprotein with anti-allergic properties, called alprogen and a novel anti-inflammatory compound, C-glucosyl chromone.

Fatty acids: It provides 4 plant steroids; cholesterol, campesterol, β-sisosterol and lupeol. All these have anti-inflammatory action and lupeol also possesses antiseptic and analgesic properties.

Nettle Leaf Extract: Scientifically termed *Urtica dioica* L. is a wild plant little known in gastronomy. However, it is a food that stands out for its iron and selenium content, as well as vitamins A, C and K and whose consumption is completely safe. Not only does nettle help in combating hair loss, it also helps in hair re-growth. Nettle leaves are rich in silica and sulphur. This helps in making hair shinier and healthier. Rinsing hair with nettle extracts and water results in re-growth of lost hair and also helps in restoring the original hair colour.

Licorice Root Extract: Licorice is an herbal extract derived from the root of the plant *Glycyrrhiza glabra* with potential anti-inflammatory, antioxidant, and antineoplastic activities. Licorice root extract contains glycoside glycyrrhizinic acid and numerous flavonoids. Glycyrrhizinic acid in licorice root extract is hydrolyzed to glycyrrhetic acid (GA); GA inhibits 11 beta-hydroxysteroid dehydrogenase, resulting in inhibition of the conversion of cortisol to the inactive steroid cortisone and elevated cortisol levels. The Licorice Root can fight off baldness and improve hair health. It is also one of the highly recommended treatments for hair loss. The pores of the scalp open up due to its mollifying properties and reduce irritation and redness resulting in hair growth.

Caffeine Powder: We also know caffeine by the IUPAC name 1, 3, 7-Trimethylpurine-2,6-dione. The main benefit of caffeine is that it can help promote hair growth straight from the root in the initial phases of hair growth. It does this through targeting a hormone called 'DHT', which causes hair loss. DHT can prevent vitamins, proteins and minerals from helping hair follicles to grow. Caffeine combats this by causing hair cells to produce more 'ATP', which is a form of energy that encourages hair to grow.

Copper Peptides GHK: is based on copper tripeptide-1. It helps enlarge hair follicles and stimulate hair growth. It is excellent in repairing and remodeling skin, and offers anti-wrinkle, anti-aging, and skin-firming benefits.

Menthol Crystals: Menthol has been found, in more recent years, to have positive effects when used as a hair growth treatment. The reason that menthol is considered helpful for hair growth is because it's known scientifically as a vasodilator. This means that it has the ability to stimulate blood circulation in the scalp and cause hair follicles to open up, leading to more hair growth. The cooling effects felt from menthol can do more than just awaken your mind—it can help awaken your scalp and body. Hair care products that contain essential oils like tea tree oil and peppermint have vasodilating effects that are found to boost hair growth over a period of time.

Propanediol 1,3: Propanediol 1,3 is a natural, green, propylene glycol alternative derived from corn sugar, used as a humectant, hair and skin conditioner, preservative booster, and a solvent with a light, non-sticky, slightly dry skin feel.

Propanediol increases hydration when used in hair and body products, and at 5%, performs better than propylene glycol and butylene glycol. When combined with glycerin, Propanediol shows a synergistic effect that reduces the tackiness of glycerin, while offering the benefits of increased levels of hydration. At levels up to 75%, it shows low potential to irritate or sensitize skin.

In surfactant systems, Propanediol increases the clarity of surfactant systems and viscosity while decreasing the amount of salt necessary to thicken a product. It improves flash foam, and produces more elegant systems with creamier lather and denser foam.

In hair care products, such as shampoo, conditioner, leave on conditioners, or styling aids, it offers a cleaner feeling after rinsing while increasing moisturization, improving detangling, reducing static, and improving wet and dry combing.

Citric Acid: Citric acid improves the scalp condition by getting rid of the dandruff and it increases the flow of blood, which in turn enhances and mends the follicles of the hair necessary for a healthy hair growth.

According to an embodiment of the present invention, there is provided in a non limiting manner a non-irritating hair care synergistic composition in the form of spray or shampoo for *Demodex* treatment of scalp which comprises ingredients as follows:

|  | Terpinen-4-ol spray | Percentage | Content (Gr) |
|---|---|---|---|
| Water | Water | 48.00 | 480.00 |
|  | Witch Hazel Hydrosol | 20.00 | 200.00 |
| Oils | Terpinen-4-ol solution (T4O) | 5.00 | 50.00 |
|  | Fractionated coconut oil | 2.00 | 20.00 |
|  | Lavender Essential Oil | 0.20 | 2.00 |
|  | Eucalyptus Essential Oil | 0.20 | 2.00 |
|  | Peppermint Essential Oil | 0.60 | 6.00 |
|  | Polysorbate 80 | 7.00 | 70.00 |
| Additives | Saw Palmetto Extract | 2.00 | 20.00 |
|  | Green Tea Extract | 1.00 | 10.00 |
|  | Aloe Vera Pure Juice | 3.00 | 30.00 |
|  | Nettle Leaf Extract | 2.00 | 20.00 |
|  | Licorice Root Extract | 1.00 | 10.00 |
|  | Caffeine Powder | 0.50 | 5.00 |
|  | Copper Peptides GHK | 0.20 | 2.00 |
|  | Menthol Crystals | 1.00 | 10.00 |
|  | Propanediol 1,3 | 5.00 | 50.00 |
|  | Citric Acid | 0.10 | 1.00 |
|  | Potassium sorbate | 0.20 | 2.00 |
|  | Geogard 221 - (Benzylalcohol-DHA) | 1.00 | 10.00 |
|  |  | 100.00 | 1000.00 |

According to another embodiment of the present invention, there is provided in a non limiting manner a non-irritating hair care synergistic composition in the form of spray or shampoo for *Demodex* treatment of scalp which comprises ingredients as follows:

|  | Terpinen-4-ol spray | Percentage | Content (Gr) |
|---|---|---|---|
| Water | Water | 38.00 | 380.00 |
|  | Witch Hazel Hydrosol | 20.00 | 200.00 |
| Oils | Terpinen-4-ol solution (T4O) | 10.00 | 100.00 |
|  | Fractionated coconut oil | 2.00 | 20.00 |
|  | Lavender Essential Oil | 0.20 | 2.00 |
|  | Eucalyptus Essential Oil | 0.20 | 2.00 |
|  | Peppermint Essential Oil | 0.60 | 6.00 |
|  | Polysorbate 80 | 12.00 | 120.00 |
| Additives | Saw Palmetto Extract | 2.00 | 20.00 |
|  | Green Tea Extract | 1.00 | 10.00 |
|  | Aloe Vera Pure Juice | 3.00 | 30.00 |
|  | Nettle Leaf Extract | 2.00 | 20.00 |
|  | Licorice Root Extract | 1.00 | 10.00 |
|  | Caffeine Powder | 0.50 | 5.00 |
|  | Copper Peptides GHK | 0.20 | 2.00 |
|  | Menthol Crystals | 1.00 | 10.00 |
|  | Propanediol 1,3 | 5.00 | 50.00 |
|  | Citric Acid | 0.10 | 1.00 |
|  | Potassium sorbate | 0.20 | 2.00 |
|  | Geogard 221 - (Benzylalcohol-DHA) | 1.00 | 10.00 |
|  |  | 100.00 | 1000.00 |

In another embodiment of the present invention, provides a method of preparing the plant based composition for *Demodex* treatment of scalp in the form of shampoo or hairspray, the method comprising the steps of:

Placing the water in the container or beaker with continuous agitation, until its total dilution;

Adding Caffeine Powder, Copper Peptides GHK and Potassium sorbate and mixing;

Adding the Menthol Crystals (Previously diluted in Propanediol 1,3) and mixing;

Adding the extracts and other additives in agitation medium;

Continuing mixing until a homogeneous mixture is obtained;

adding the Essential oils, Oils and the Polysorbato 80 in another container and mixing continuously until a homogeneous mixture is obtained;

Slowly adding the oil mixture (Essential oils+Oil+Polysorbato 80) in the Toner;

Mixing continuously until obtaining a homogeneous mixture.

The pH of the above mixture is maintained at a range of 4.5 to 6. Further, the pH can be regulated with one or two drops of citric acid (Solution 50%), stirring to mix well.

It is to be understood that the aforementioned components and volumes as well as steps are only exemplary and that various arrangements are possible in other embodiments.

While there have been shown and described and pointed out the fundamental novel features of the invention as applied to the preferred embodiments, it will be understood that the foregoing is considered as illustrative only of the principles of the invention and not intended to be exhaustive or to limit the invention to the precise forms disclosed. Obvious modifications or variations are possible in light of the above teachings. The embodiments discussed were chosen and described to provide the best illustration of the principles of the invention and its practical application to enable one of ordinary skill in the art to utilize the invention in various embodiments and with various modifications as are suited to the particular use contemplated All such modifications and variations are within the scope of the invention as determined by the appended claims when interpreted in accordance with the breadth to which they are entitled.

The invention claimed is:

1. A plant based synergistic hair care composition for treatment of *Demodex* of scalp, the said composition comprising essentially of:
   a) an effective amount of Terpinen-4-ol solution wherein said effective amount of said Terpinen-4-ol is 5.00% by volume;
   b) an effective amount of fractionated coconut oil wherein said effective amount of said Fractionated coconut oil is 2.00% by volume;
   c) an effective amount of Lavender oil wherein said effective amount of said Lavender oil is 0.20% by volume;
   d) an effective-amount of Eucalyptus oil wherein said effective amount of said Eucalyptus oil is 0.20% by volume;
   e) an effective amount of Peppermint oil wherein said effective amount of said Peppermint oil is 0.60% by volume;
   f) an effective amount of polysorbate 80 wherein said effective amount of said polysorbate 80 is 7.00% by volume;
   g) an effective amount of saw palmetto extract wherein said effective amount of said saw palmetto extract is 2.00% by volume;
   h) an effective amount of Green Tea Extract wherein said effective amount of said Green Tea extract is 1.00% by volume;
   i) an effective amount of Aloe Vera Pure Juice wherein said effective amount of said Aloe Vera Pure Juice is 3.00% by volume;
   j) an effective amount of Nettle Lear Extract wherein said effective amount of said Nettle Leaf Extract is 2.00% by volume;
   k) an effective amount of Licorice Root Extract wherein said effective amount of said Licorice Root Extract is 1.00% by volume;
   l) an effective amount of Caffeine Powder wherein said effective amount of said Caffeine Powder is 0.50% by volume;
   m) an effective amount of Copper Peptides GHK wherein said effective amount of said Copper Peptides GHK is 0.20% by volume;
   n) an effective amount of Menthol Crystals wherein said effective amount of said Menthol Crystals is 1.00% by volume;
   o) an effective amount of Propanediol 1.3 wherein said effective amount of said Propanediol 1,3 is 5.00% by volume;
   p) an effective amount of citric acid wherein said effective amount of said critic acid is 0.10) % by volume;
   q) an effective amount of Potassium sorbate wherein said effective amount of said Potassium sorbate is 0.20% by volume;
   r) an effective amount of Benzyl alcohol wherein said effective amount of said Benzyl alcohol is 1.00% by volume;
   s) an effective amount of Witch hazel hydrosol wherein said effective amount of said Witch hazel hydrosol is 20.00% by volume; and
   t) an effective amount of water wherein said effective amount of said water is 48% % by volume.

2. The plant based synergistic hair care composition of claim 1, wherein the amount of Terpinen-4-ol is 10.00% by volume, polysorbate 80 is about 12.00% by volume and water is 38.00% by volume.

3. A method of producing the plant based synergistic hair care composition for treatment of *Demodex* of scalp comprising the steps of:
   a) placing the water in the container or beaker with continuous agitation, until its total dilution;
   b) adding Caffeine Powder, Copper Peptides GHK and Potassium sorbate and mixing;
   c) adding the Menthol crystals, previously diluted in 1,3-propanediol and mixing;
   d) adding the extracts including Saw palmetto, green tea, nettle leaf and licorice root and other additives including aloe vera pure juice in agitation medium;
   e) continuing mixing until a homogenous mixture is obtained;
   f) adding the Essential oils including Lavender, Eucalyptus and peppermint, Oils including fractionated coconut oil and the Polysorbate 80 in another container and mixing continuously until a homogenous mixture is obtained;
   g) slowly adding the oil mixture of step (f) in the container; and then
   h) mixing continuously until obtaining a homogenous mixture.

4. The method of claim 1, wherein the pH of the mixture is maintained in a range between 4.5 to 6.

5. The method of claim 1, wherein the pH of the mixture is regulated by adding 1-2 drops of citric acid 50% solution, stirring to mix well.

* * * * *